(12) United States Patent
Mantelmacher

(10) Patent No.: US 6,793,682 B1
(45) Date of Patent: Sep. 21, 2004

(54) SURE-FIT PROSTHETIC ATTACHMENT SYSTEM

(76) Inventor: H. Lee Mantelmacher, 3704 Ashley Way, Owings Mills, MD (US) 21117

( * ) Notice: Subject to any disclaimer, the term of this patent is extended or adjusted under 35 U.S.C. 154(b) by 0 days.

(21) Appl. No.: 10/405,757

(22) Filed: Apr. 1, 2003

(51) Int. Cl.$^7$ .................................................. A61F 2/80
(52) U.S. Cl. .......................................... 623/36; 623/33
(58) Field of Search ............................. 623/33–37, 57; 602/61–63; 403/286, 299, 341

(56) References Cited

U.S. PATENT DOCUMENTS

| | | | | | |
|---|---|---|---|---|---|
| 3,922,727 | A | * | 12/1975 | Bianco | 623/24 |
| 4,842,608 | A | * | 6/1989 | Marx et al. | 623/33 |
| 4,872,879 | A | * | 10/1989 | Shamp | 623/36 |
| 5,211,667 | A | * | 5/1993 | Danforth | 623/35 |
| 5,529,575 | A | * | 6/1996 | Klotz | 623/33 |
| 5,571,209 | A | * | 11/1996 | Brown, Sr. | 623/33 |
| 5,651,792 | A | * | 7/1997 | Telikicherla | 623/36 |
| 5,653,766 | A | * | 8/1997 | Naser | 623/33 |
| 6,368,357 | B1 | * | 4/2002 | Schon et al. | 623/37 |
| 6,666,894 | B2 | * | 12/2003 | Perkins et al. | 623/36 |

FOREIGN PATENT DOCUMENTS

DE 4321182 C1 * 12/1994 ............. A61F/2/78

* cited by examiner

Primary Examiner—Alvin Stewart
(74) Attorney, Agent, or Firm—Law Office of Royal W. Craig

(57) ABSTRACT

An anchoring system for a transtibial or transfemoral (above or below the knee) prosthesis. The system includes a liner for enveloping an amputee limb. The liner has a buckle suspended toward the upper end, and a corresponding strap fixedly attached toward the bottom end of the liner. The anchoring system also includes a containment socket for seating the liner. The containment socket has a first slot there through at a position corresponding to the buckle of the liner. The socket also has a second slot there through at a position corresponding to the strap. In use, the patient first applies the liner, then inserts the liner into the socket with the fastening strap and buckle protruding out through the respective slots. The fastening strap is then threaded up through the buckle (the strap running upward along the side of the socket) and is inserted there through. The patient pulls down on the strap and it works by pulley action to draw the liner down into the socket until the liner is securely seated in the socket. When fully seated, the fastening strap is secured. The foregoing forms a suspension which holds the prosthesis on securely, and yet can easily be adjusted to reseat the limb.

7 Claims, 8 Drawing Sheets

SURE-FIT PROSTHETIC ATTACHMENT SYSTEM

BACKGROUND OF THE INVENTION

1. Field of the Invention

The present invention relates to prosthetics and, more particularly, to an anchoring system for post-operative prosthetic devices for above-the-knee amputation patients.

2. Description of the Background

There are a variety of different types of prosthetic devices for patients that have had either transfemoral (above-knee) or transtibial (below the knee) amputation. Typically, post-operative prosthetic devices for either type of amputation patients begin with a liner, which is rolled on to the residual limb. The liner is a soft, stretchy material that acts as an interface with the prosthetic.

Once the liner is on, the residual limb then slides into a hard socket. This socket is specially made to fit and can be made out of a variety of materials.

The hard socket for a transfemoral prosthesis has a knee joint connected to it, and the more fluid and natural the movement of the knee the better. Transtibial prosthetics have no knee joint. In both cases (with or without a knee joint) there typically is an aluminum or carbon fiber tube to which a foot module is connected.

For example, FIG. 1 is a prior art perspective view of the prosthetic device set forth in U.S. Pat. No. 5,653,766 to Naser issued Aug. 5, 1997. The illustrated prosthetic device 20 includes a generally cylindrical socket 24 having an opening for receiving an amputated limb. The socket 24 is closed at the other end, and is mounted on a bendable knee joint. Once the limb is properly received within the socket 24, straps 38 are adjusted so that a secure fit is achieved. The patient then is able to walk using the prosthetic device 20.

With all transfemoral and/or transtibial prosthetics (above & below the knee), it is very important that the socket be securely fitted to the limb and secured in place. Stability is a common problem as many existing anchoring systems use a single attachment point to hold the residual limb in place, and this typically leads to extraneous pivoting, rotation and shift during ambulation. Moreover, it is important to be able to easily adjust the anchoring system periodically inasmuch as the mass of the limb may change significantly over the course of a day. Consequently, there should be some means for adjustment on the fly. The above-referenced '766 patent uses a radial pressure-fit imposed by tightening two belts. However, this tends to squeeze the limb and adds to discomfort, Moreover, the radial pressure tends to pop the limb out of the socket over the course of a day.

The well-known ICEX Socket System uses a lanyard kit as a docking and locking mechanism. The socket has a distal pin that docks with the prosthesis. A lanyard is connected to the liner through a slot in the bottom of the socket. The lanyard is pulled to allow the patient's residual limb, which is enclosed in the silicone liner, to be drawn into the socket by the lanyard. The lanyard is then anchored to the front of the socket. The lanyard has the advantage of allowing for adjustment of position within the ICEX Socket. If the limb changes position because of volume change and the distal migration of the limb into the socket, the prosthesis can easily be adjusted by the lanyard to compensate. The lanyard method of donning the socket also significantly reduces pain directly related to the donning process with a pin-locking mechanism. However, it has been found that many amputees lack thee room for, are unable to tolerate, or have difficulty engaging the distal pin. Others complain of pain associated with engagement of the pin.

Coyote Systems® sells the Summit Lock for those who cannot tolerate the "pull" associated with distal pin lock and lanyard suspension methods. The Summit Lock eliminates the pin, and instead uses a ratchet-type ski buckle assembly (a strip with multiple lock teeth), which is attached to the lateral aspect of the liner at about ischial level. The tab is fed through a hole in the socket and engages in the externally mounted lock. Positioning the tab through the socket wall controls rotation. Mounting the lock externally makes it easy to engage and reduces jamming. While the Summit Lock is a more flexible design, it does not provide as secure a fit. The Summit Lock only holds the limb in place from the top of the socket and is prone to shift. In addition, the patient cannot tighten the fit of the liner in the socket from a sitting position but must put his/her full weight onto the prosthetic.

There remains a significant commercial need for a prosthetic anchoring system which provides a stable anchor for the liner with topside and lower attachment which prevents all extraneous up and down motion, pivoting, rotation and shift during ambulation, and which allows a patient to easily tighten/readjust the fit of the liner in the socket from a sitting position.

SUMMARY OF THE INVENTION

Accordingly, it is an object of the present invention to provide a prosthetic anchoring system which increases the stability of the liner anchor using a combination of top-side and lower attachments to prevents all extraneous up and down motion, pivoting, rotation and shift.

It is another object to eliminate the need for distal pin locks, and yet allow a patient to easily anchor the liner in the socket, and to easily readjust/tighten the fit of the liner in the socket from a sitting position.

It is still another object to provide a prosthetic anchoring system which is simple, inexpensive and highly effective, and which allows extremely convenient on-the-fly adjustment of the limb/liner seating to improve the fit despite changes in the size of the limb over the course is of a day.

In accordance with the foregoing object, the present device comprises an anchoring system for a transfemoral and/or transtibial prosthesis, comprising a liner for enveloping an amputee limb. The liner has a buckle suspended toward the upper end, and a corresponding strap fixedly attached on the bottom end of the liner. The anchoring system also includes a containment socket for seating the liner. The containment socket has a pair of slots there through at positions corresponding to the buckle and strap of the liner, respectively. To apply the anchoring system, the patient first applies the liner to his/her limb. The liner is then inserted into the socket with the fastening strap and buckle protruding out through the respective slots. The fastening strap is then threaded up through the buckle (running upward along the side of the socket) and are inserted there through. The patient pulls down on the strap and it works by pulley action to draw the liner down into the socket until the liner is securely seated in the socket. When fully seated, the fastening strap is secured to itself by Velcro.

The foregoing forms a suspension which holds the prosthesis on. Moreover, the fastening straps through slots absolutely prevent lateral shift as well as rotation. On the other hand, the patient need only readjust the Velcro closure to ad just the position of the limb within the socket. Thus, if the limb changes position because of volume change and the distal migration of the limb into the socket, the prosthesis can easily be adjusted to compensate.

BRIEF DESCRIPTION OF THE DRAWINGS

Other objects, features, and advantages of the present invention will become more apparent from the following detailed description of the preferred embodiment and certain modifications thereof, in which.

DETAILED DESCRIPTION OF THE PREFERRED EMBODIMENTS

Figure 1:
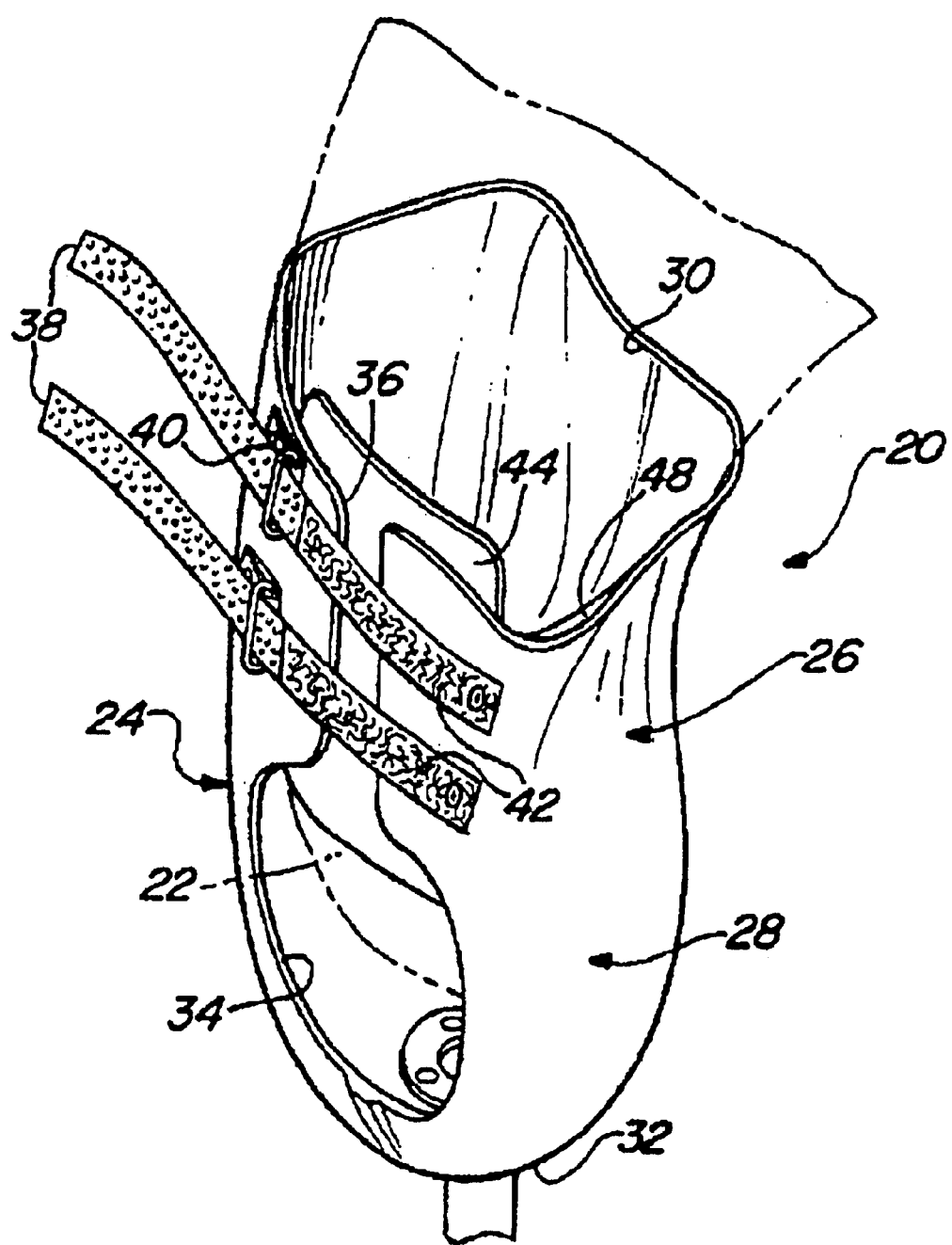
FIG. 1 is a prior art perspective view of the prosthetic device set forth in U.S. Pat. No. 5,653,766 to Naser.
Figure 2:
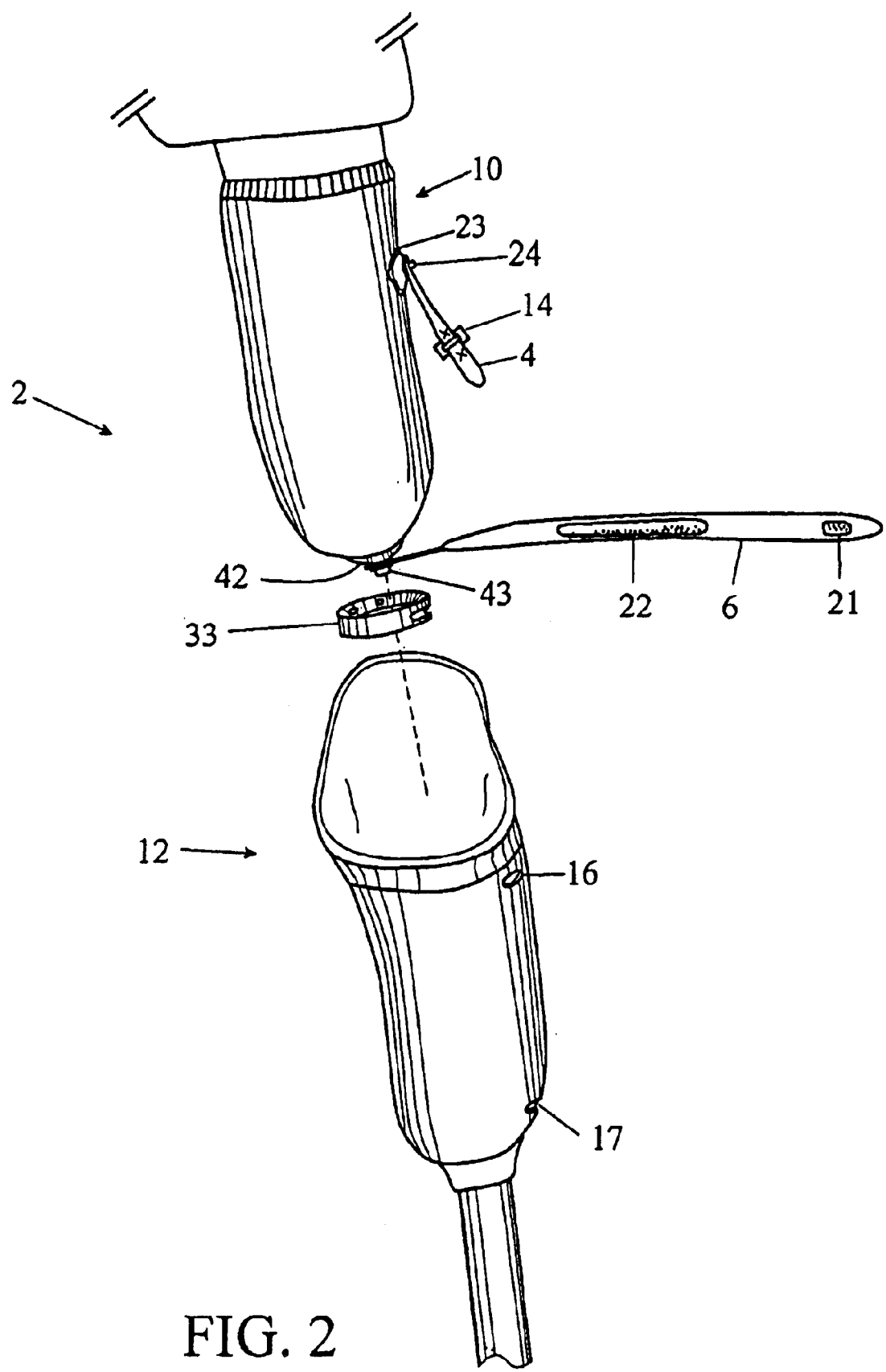
FIG. 2 is a perspective illustration of the sure-fit prosthetic anchoring system 2 according to the present invention.

FIG. 2 is a perspective illustration of the sure-fit prosthetic anchoring system 2 according to one embodiment of the present invention. The anchoring system 2 is adapted for a patient that has undergone a limb reduction surgery resulting in an above-the-knee amputation.

The anchoring system 2 generally includes a commercially-available liner 10 equipped with upper and lower strap-anchors 4, 6, respectively, in accordance with the present invention. The upper strap anchor 4 is pivotally attached at one end by grommet 24 to a reinforcement plate 23, plate 23 being a plastic member that is sewn and/or bonded peripherally onto the liner 10 at an upper outside position as shown. Presently, the grommet 24 comprises two screw-together sections having 1" flanges which sandwich the plate 23 and upper strap 4 together. The other end of upper strap 4 bears a buckle 14 with a short length of extension strap past the buckle 14 to provide a finger-grip. The extension strap past the buckle 14 may be a short length of strap or plastic attached to the buckle itself, a slightly longer length sewn to the upper strap 4, or an even longer length of strap/plastic attached by the grommet directly to the reinforcement plate 23, in all cases serving to provide the user with a finger grip to pull the liner 10 down.

In addition, a lower strap 6 is attached at one end to the bottom of the liner 10. The liner 10 fits within a molded socket 12 and rests upon a centering cup 33. The socket 12 is formed with at least one slot 16 passing through an upper side (at the outside of the limb) for allowing the upper strap 4 and buckle 14 to pass outwardly therefrom. The socket 12 is also formed with one lower slot 17 at the bottom and aligned with the upper socket 16 for allowing the lower strap 15 to pass outwardly therefrom.

The lower fastening strap 6 has a section 21 of hook-and-loop material at the distal end, and a mating section 22 of hook-and-loop material running lengthwise along its midsection. In use, the patient would first apply liner 10 to limb. The liner 10 is then inserted into the socket with lower fastening strap 6 threaded through centering cup 33 out through lower slot 17, and upper strap 4 with buckle 14 passing out through upper slot 16. The lower fastening strap 6 is then threaded up through the protruding buckle 14 and downwardly, and the strap 6 is pulled tight until the liner 10 is securely seated in the socket 12 atop cup 33. The fastening strap 6 is secured onto itself by joining the sections 21, 22 of hook-and-loop material. The foregoing forms a suspension which holds the prosthesis on and absolutely prevents lateral movement, pivotal shifting, and rotation. On the other hand, the simple Velcro®-attached strap 6 allows for convenient adjustment of the position of the limb within the socket 12. Thus, if the limb changes position because of volume change and the distal migration of the limb into the socket, the prosthesis can easily be adjusted by adjusting straps 4, 6 to compensate. The particular components of the sure-fit anchoring system 2 will now be described in more detail with reference to FIGS. 3–6.

Figure 3:
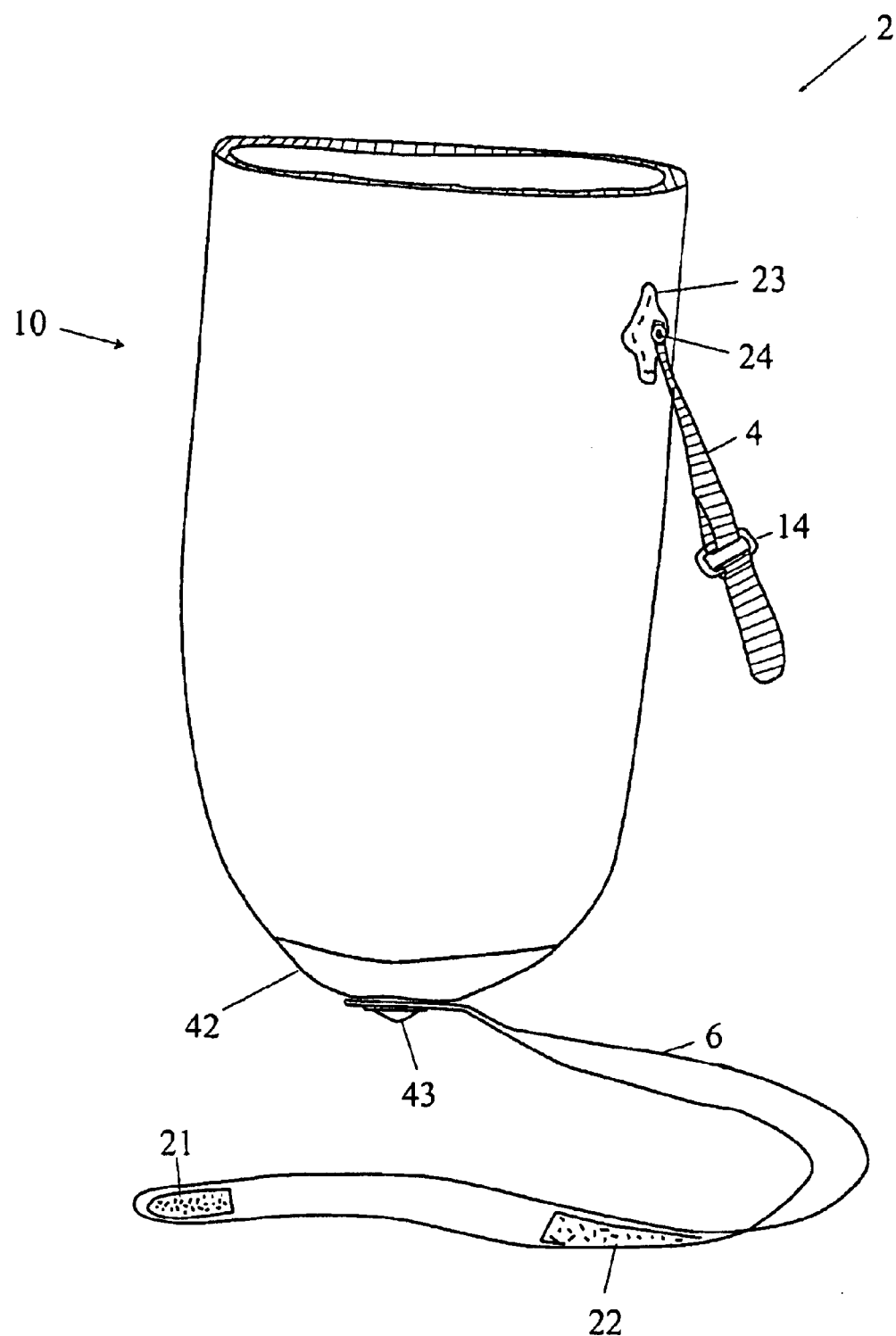
FIG. 3 is a close-up perspective view of the liner 10 as in FIG. 2.

FIG. 3 is a close-up perspective view of the liner 10. Liner 10 is largely a standard transfemoral or transtibial suspension liner designed for amputees with amputations along the length of the tibia or femur. There are a variety of commercially-available suspension liners which will suffice, provided that they afford good suspension independent of volume fluctuations and provide a comfortable anatomical fit. These liners are typically formed of silicone or a gel blend with a fabric shell, and they are equipped with a threaded socket assembly 42 at the bottom end (typically intended for screw-insertion of a pin such as utilized in prior art pin securing assemblies). In accordance with the present invention, the otherwise conventional liner is modified by tethering buckle 14, via upper strap 4, on the outwardly facing side of the liner 10. Strap 4 is secured to the liner 10 by first sewing and/or gluing the reinforcement pad 23 peripherally to the shell of the liner 0, and then passing a grommet-post 24 through the tip of the upper strap 4 and through the pad 23, thereby pivotally anchoring strap 4 thereto. Strap 4 is a short length (approximately 6") of braided Nylon or Dacron strap that is looped around one side of a rectangular buckle 14, thereby suspending buckle 14 approximately 3–5" downward from post 24. The buckle 14 is a simple rectangular stirrup-type stainless fixture. It should be understood that alternate embodiments are possible without departing from the scope and spirit of the invention, the point being that the tethered buckle 14 must be suspended by a short distance. Preferably, a short length (approximately 1–2") of strap material is attached to the opposing side of buckle 14 in a like manner and extends therefrom to provide a finger-grip to facilitate insertion of the strap 4 and buckle 14 through the upper slot 16 in socket 12.

In addition to the upper strap 4 with buckle 14, the liner 10 is equipped with a lower fastening strap 6 comprising approximately a 2' length of Nylon or Dacron braided strap attached at one end to the bottom of liner 10. As stated previously, the preferred liner 10 is equipped with a threaded socket assembly 42 at the bottom end which includes a threaded metal screw-socket embedded in a concave rubber cup 42 which is then epoxied and/or sewn, or otherwise fixedly attached to the distal end of the liner 10. A screw 43 is passed through the strap 6 and is screwed into the threaded socket assembly 42 to pivotally anchor the strap 4 thereto. The lower fastening strap 6 has a section 21 of hook-and-loop material attached to the distal end, and a mating section 22 of hook-and-loop material running lengthwise along its mid-section for attaching strap 6 onto itself around buckle 14.

Figure 4:
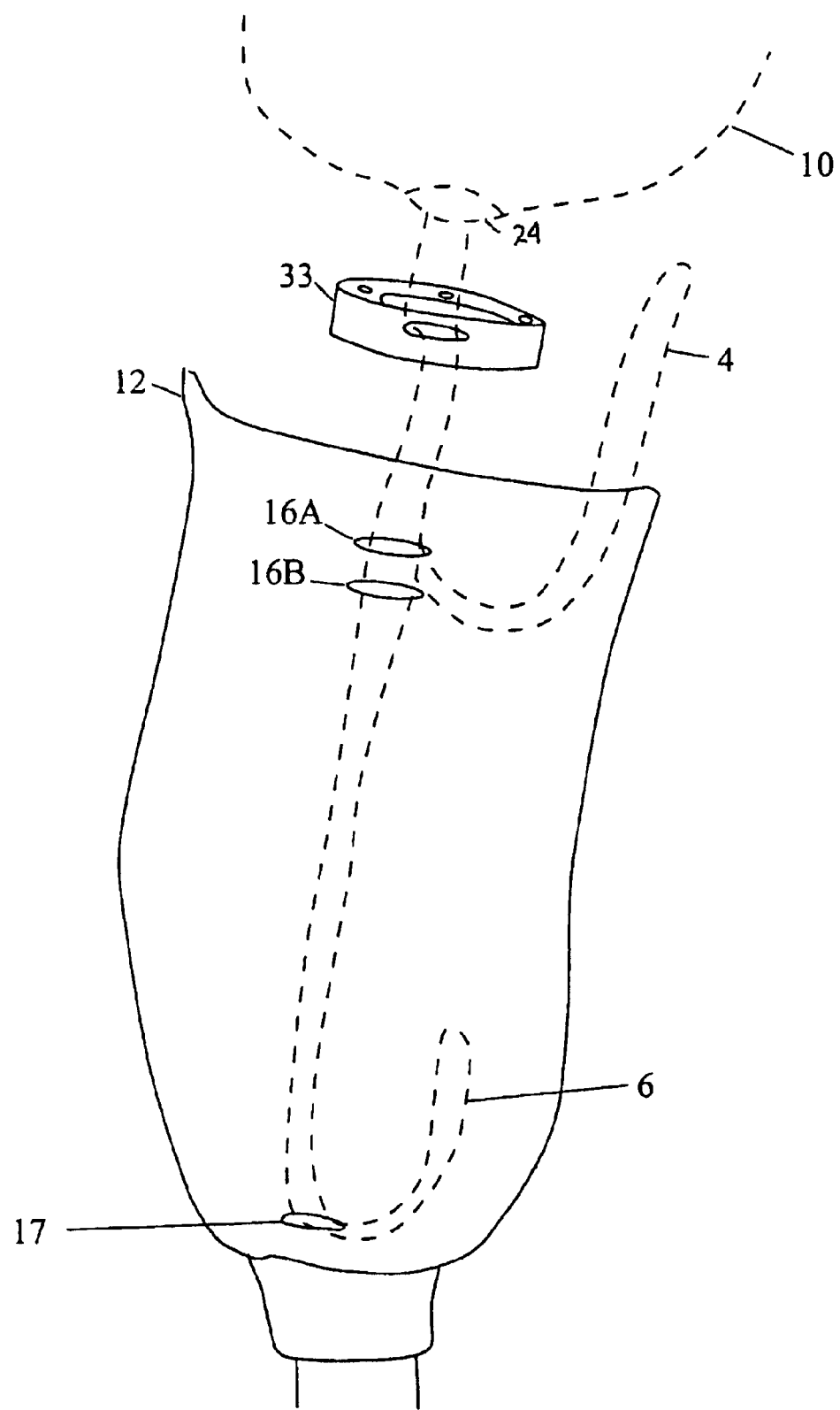
FIG. 4 is a close-up perspective view of the socket 12 as in FIG. 2.

FIG. 4 is a close-up perspective view of the socket 12. Socket 12 is generally a conventional socket formed of flexible plastic that is vacuum formed. The socket 12 made in a custom-fitted component that is made in a conventional manner of a copolymer plastic, plastic polypropylene, polyester, acrylic/epoxy resin. The socket 12 may be vacuum formed or thermoformed by heating the plastic material and forming it over a mold. In accordance with the present invention the socket 12 is formed with at least one pass-through slot 16 upwardly along the outside. At least one pass-through slot 16 is required, although two or more facilitate adjustment. Thus, in place of the single slot shown in FIG. 2, a parallel pair of pass-through slots 16A & 16B (or even a larger series) may be used as shown in FIG. 4, the pair being positioned upwardly along the opposing sides of the socket 12. Whether a single slot 16, a pair 16A & 16B, or a series, the slots are spaced with respect to the liner 10 inserted therein so that they are aligned with the upper strap 4. Specifically, when the liner 10 is fully inserted at least one pass-through slot 16 should be even with the grommet-post 24 on liner 10. Other pass-through slots 16B, C . . . may be positioned slightly above or below for adjustment. This allows the tethered buckle 14 to be inserted directly through a selected slot 16A, 16B (as appropriate) from inside the socket 12 to outside, such that downward tension on strap 4 anchors the grommet-post 24 directly against the slot. In addition to the upper slot(s) 16, a lower pass-though slot 17 is positioned downwardly along the same side of the socket 12. The pass-through slot 17 is spaced with approximately a 2" offset with respect to the bottom of the socket 12. This way, when the liner 10 is fully inserted the pass-through slot 17 allows the lower fastening strap 15 to be inserted there through. The outer end of the socket 12 is adapted to be connected to a conventional, bendable knee joint (a variety of which are presently available).

Figure 5:
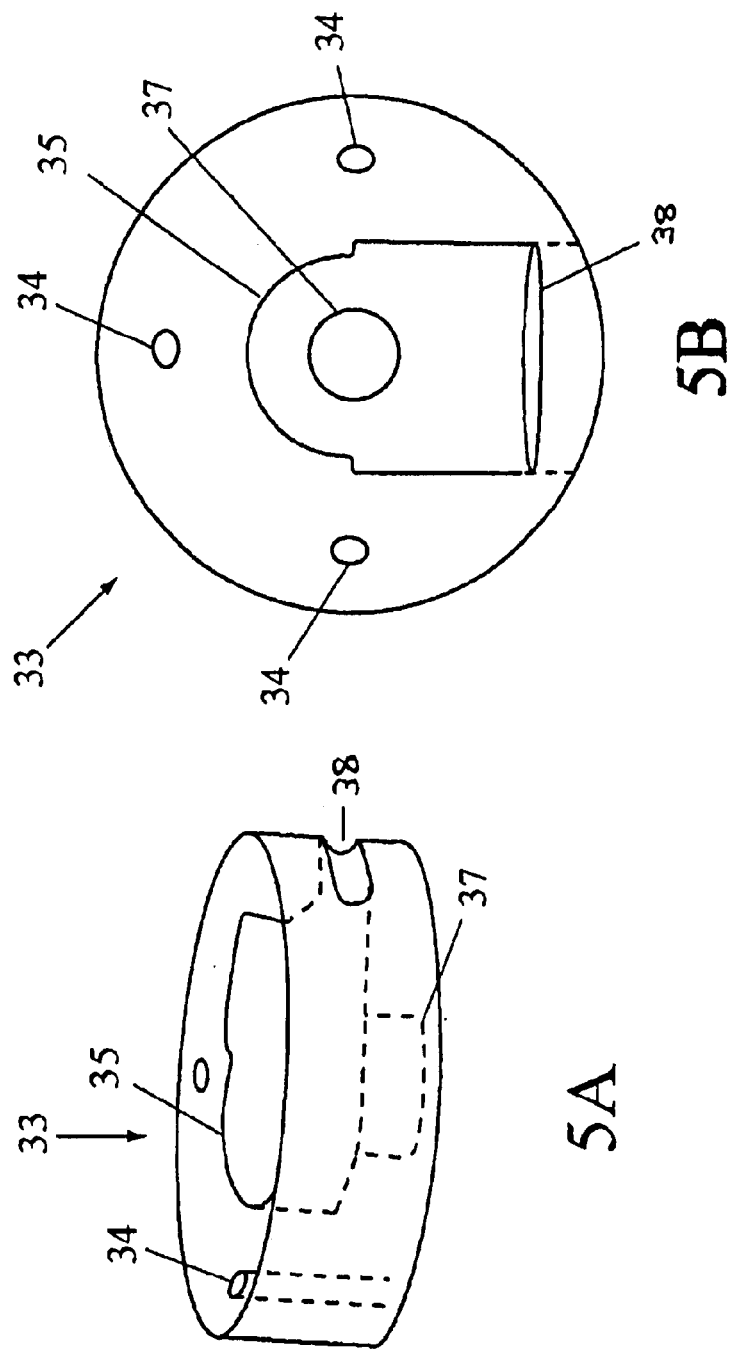
FIG. 5 is a composite perspective view and top view, respectively, of the cup insert 33 as in FIG. 2.

FIG. 5 is a composite perspective view and top view, respectively, of the centering cup insert 33 as in FIG. 2 which is attached internally to the bottom center of the socket 12. The centering cup 33 is a puck-like member preferably formed of Delrin®, aluminum, or other sturdy material. Centering cup 33 is formed with a partially concave upper surface leading into an alcove 35. The concave upper surface helps to seat and center the liner 10. The alcove 35 is semi-circular (on one side) with a pronounced indentation 37 in the center for seating the head of screw 43 on the liner 10. The alcove 35 continues through the other side of insert 33 forming a slot 38 through which the lower fastening strap 6 is passed. Through-bores 34 are formed axially through the insert 33 to allow screw-attachment through the socket 12 into the base of the bendable knee joint (transfemoral) or the base of the shaft (transtibial), either of which are typically attached directly beneath the socket 12. Alternatively, the through-bores 34 may be eliminated and the centering cup 33 instead formed with a downwardly threaded hub for screw-attachment to the underlying base beneath socket 12.

Figure 6:
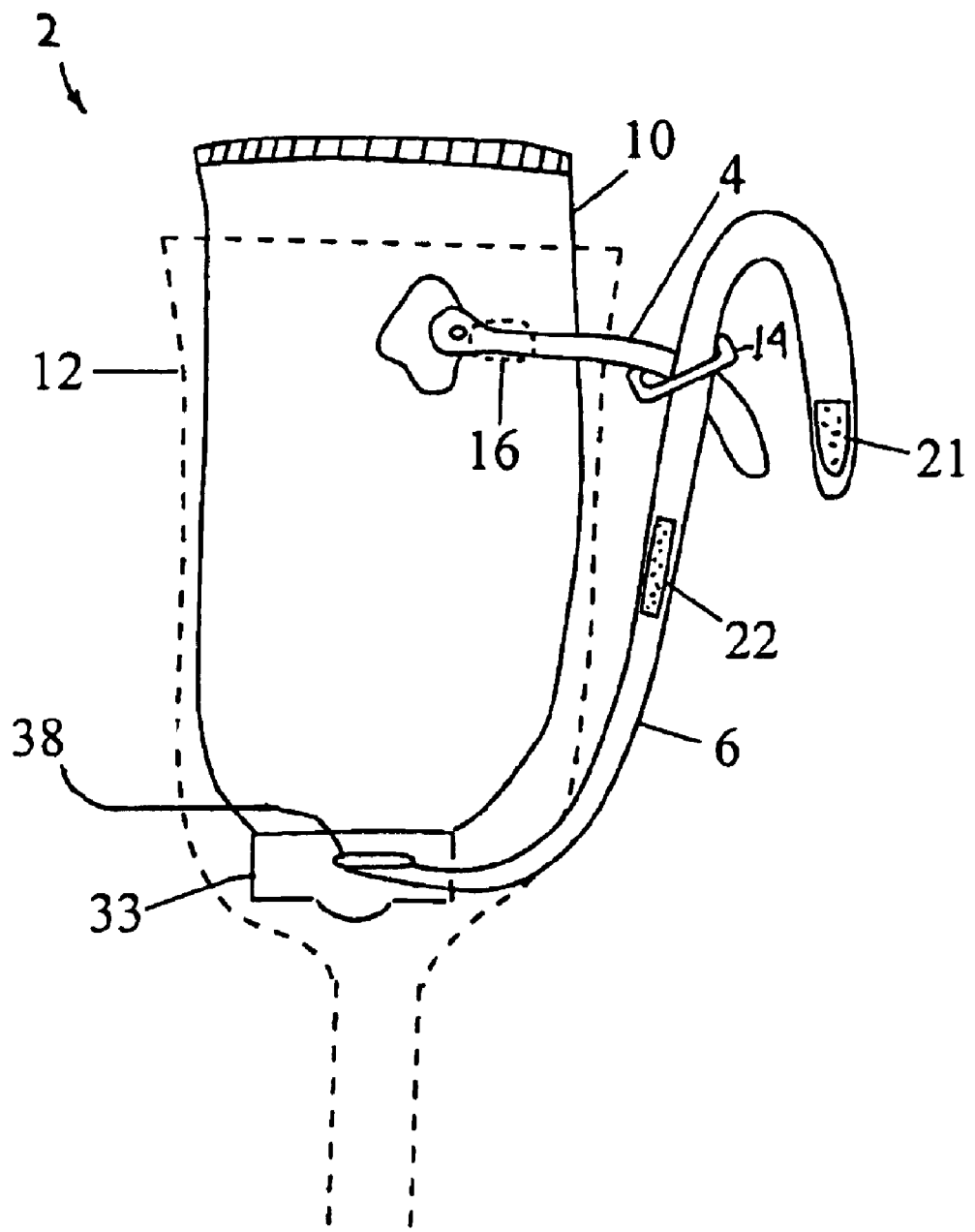
FIG. 6 is a perspective illustration showing the method of attaching the sure-fit prosthetic anchoring system 2 according to the present invention.

FIG. 6 is a perspective illustration showing the method of attaching the sure-fit prosthetic anchoring system 2 according to the present invention. To apply the anchoring system 2, the patient first applies the liner 10 to his/her residual limb. The liner 10 is then partially inserted into the socket 12 until lower fastening strap 6 can be threaded through the slot 38 in centering cup 33 and on outward through the lower slot 17 through socket 12. In addition, the upper is fastening strap 4 and buckle 14 are passed outward through slot 16. The lower fastening strap 6 is then threaded up through the buckle 14 (strap 6 running upward along the side of the socket 12) and is inserted there through. The patient pulls down on the distal end of lower strap 6 which works by pulley action to draw the liner 10 down into the socket 12 until the liner 10 is securely seated in the socket 12. When fully seated the lower fastening strap 6 is secured to itself by joining the sections 21, 22 of hook-and-loop material.

The foregoing forms a suspension which holds the prosthesis on. Moreover, the fastening strap 6 through lower slot 17 forms a first anchoring point, and the upper strap 4 through upper slot 16 forms a second anchoring point, the combination of the two anchoring points serving to absolutely prevent lateral movement, pivotal and proximal shift, and rotation. On the other hand, the patient need only readjust the Velcro closure to adjust the position of the limb within the socket 12. Thus, if the limb changes position because of volume change and the distal migration of the limb into the socket, the prosthesis can easily be adjusted to compensate.

Once the limb is properly received within the socket 12 and the straps 4, 6 are appropriately adjusted so that a secure fit is achieved. The patient then is able to walk using the prosthetic device.

Figure 7:
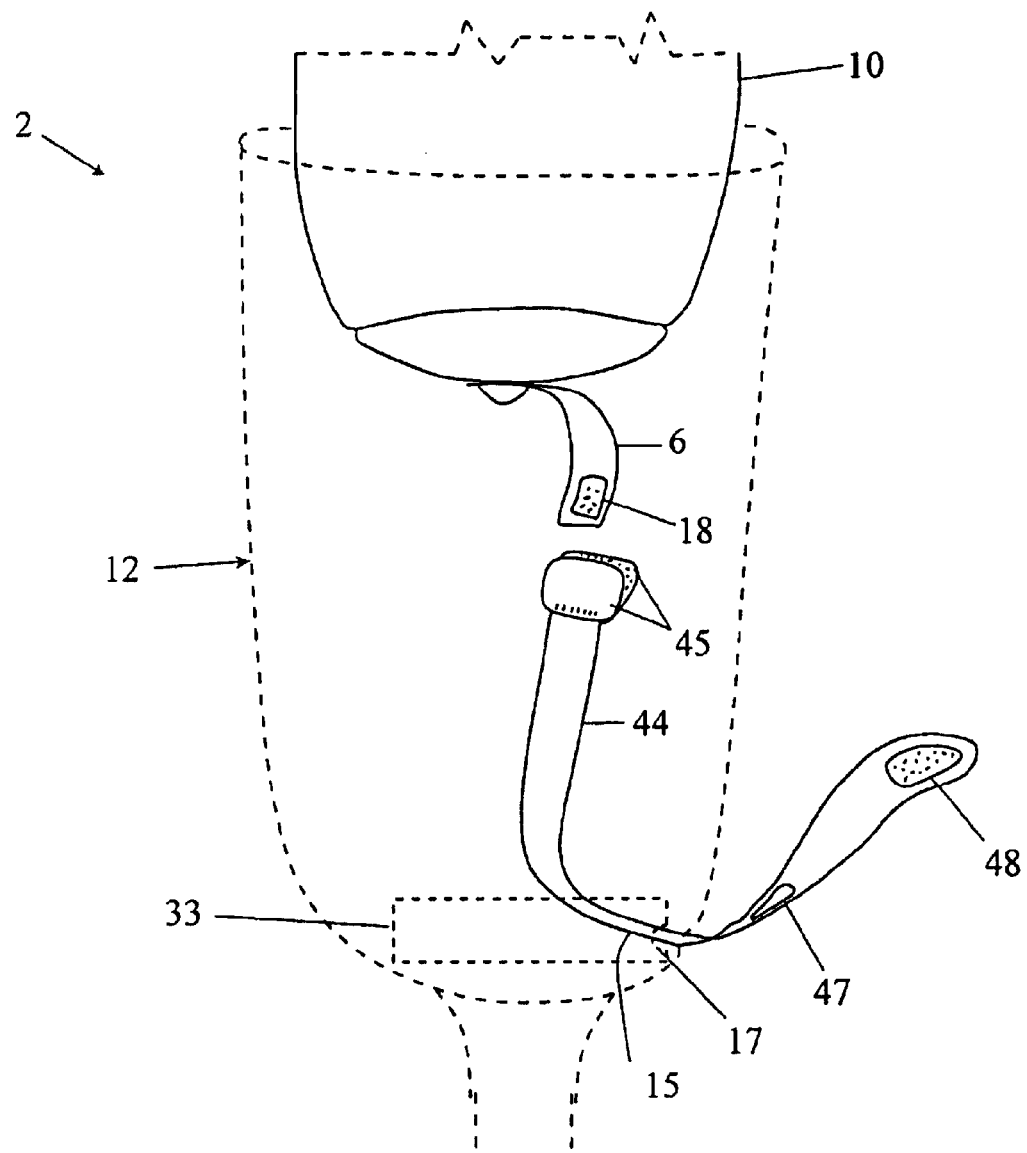
FIG. 7 is a perspective illustration of an optional extension strap 44 which can be used to simplify the attachment process for patients who lack upper-body mobility.

FIG. 7 is a perspective illustration of an optional extension strap 44 which can be used to simplify the attachment process for patients who lack upper-body mobility. Extension strap 44 essentially replaces the majority of the above-described lower strap 6 but can be left in place in centering cup 33 to avoid having to thread strap 6 through cup 33 each time the prosthetic is applied. In this case, strap 6 is substantially shortened and a section of loop material 18 is sewn to each face at the distal end. The extension strap comprises a length of woven Nylon or Dacron (or similar material) belt with a clam-shell closure 45 at one end. The other end of extension strap 44 substantially conforms to that of lower strap 6, with mating sections of hook and loop material 47, 48 attached thereto. The clam-shell closure 45 further comprises two small plastic or leather patches attached at the end of extension strap 44 and able to close upon themselves. The closure patches 45 at the end of extension strap 44 are equipped with opposing sections of hook material on their inner faces for a sandwich-type attachment to the loop material 18 at the end of strap 6. In use, the patient again applies the liner 10 to his/her residual limb. The liner 10 is then partially inserted into the socket 12. The extension strap 44 is already inserted through the centering disk 33 and outward through slot 38 and the socket 12 as shown. Next, the clamshell closure 45 of extension strap 44 is closed upon the loop 18 of strap 6, essentially forming an elongate strap which is pre-threaded and avoids excessive bending over. Just as before, the upper fastening strap 4 and buckle 14 are passed outward through slot 16 in socket 12. The extension strap 44 is then threaded up through the buckle 14 (strap 44 running upward along the side of the socket 12) and is inserted there through. The patient pulls down on the distal end of extension strap 44 which works by pulley action to draw the liner 10 down into the socket 12 until the liner 10 is securely seated in the socket 12. When fully seated, the extension strap 44 is secured to itself by joining the sections 47, 48 of hook-and-loop material.

The prosthetic anchoring system 2 described herein increases the stability of the liner anchor using the combined top-side and lower attachments to prevent all extraneous up and down motion, pivotal and proximal shift, and rotation.

It avoids the need for distal pin locks, and yet allows the patient to easily anchor the liner 10 in the socket 12, and to easily readjust/tighten the fit of the liner 10 in the socket 12 from a convenient sitting position.

Figure 8:
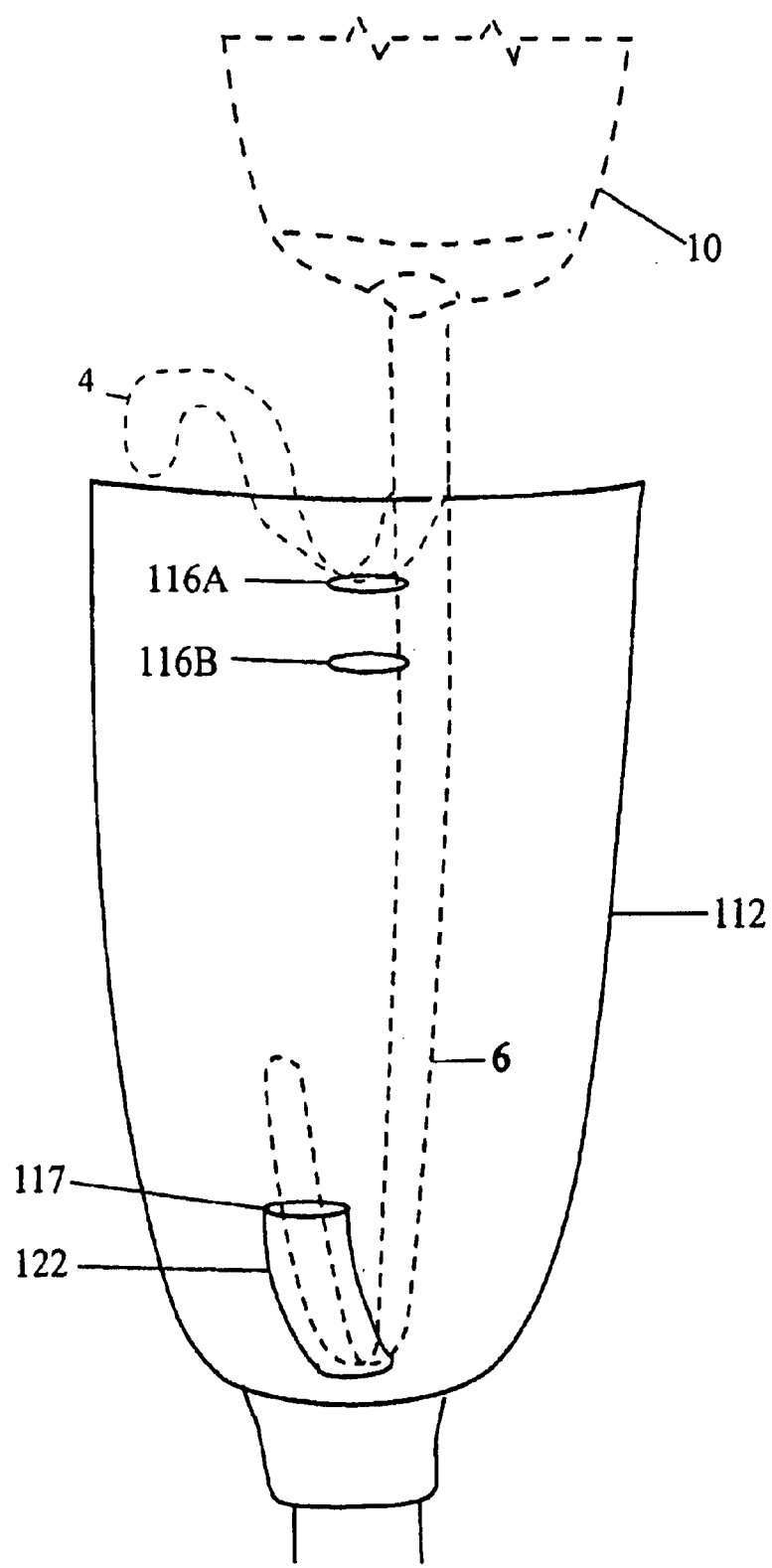
FIG. 8 is a perspective view of an alternative embodiment of the socket 120 similar to FIG. 2 but modified with a slot 122 to avoid the need for centering cup 33.

FIG. 8 is a perspective view of an alternative embodiment of the socket 112 similar to that of FIG. 2 but modified slightly with a slot 122 to avoid the need for centering cup 33. If the prosthetic anchoring system is to be employed without centering cup 33 (such as, for instance, The liner 10 is exactly as shown and described with reference to FIG. 3 (a standard transfemoral or transtibial suspension liner designed with upper strap 4 and lower strap 6). However, without centering cup 133 the socket 112 must be thermoformed with a clearance channel 122 to provide enough clearance to be able to thread the lower strap 6 outward. The clearance channel 122 is a raised channel for seating strap 6, and channel 122 runs to the clearance slot 17 which is (as before) located upwardly along the outside.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. An anchoring system for a prosthesis, comprising:
   a liner for enveloping an amputee limb, said liner having a first strap attached at one end to an upside of said liner and suspending a buckle from the other end, and a second strap attached at one end downwardly an said liner and having a closure at its other end to allow it to be fastened back upon itself;
   socket for receiving said liner, said socket having a first slot there through at a position corresponding to the first strap and a second slot there through at a position corresponding to said second strap when the liner is seated in said socket;
   whereby said liner may be securely anchored in said socket with the first strap and buckle inserted through the first slot and the second strap threaded through the second slot, the second strap inserted through the buckle, tightened, and closed upon itself to form a suspension fit which prevents lateral, pivotal and proximal shift.

2. The anchoring system according to claim 1, further comprising a centering cup seated in said socket and for seating said liner thereon.

3. The anchoring system according to claim 2, wherein said centering cup is concave to center the liner.

4. The anchoring system according to claim 3, wherein said centering cup is formed with a sidelong groove to pass said second strap.

5. The anchoring system according to claim 1, wherein said second strap further comprises a first segment attached to said liner and a second segment removably attached to said first segment.

6. The anchoring system according to claim 1, wherein the closure on said second strap comprises mating sections of hook and loop material.

7. The anchoring system according to claim 1, wherein the socket has a series of first slots there through at adjustable positions corresponding to the first strap.

\* \* \* \* \*